United States Patent
Dahme et al.

(10) Patent No.: US 10,161,919 B2
(45) Date of Patent: Dec. 25, 2018

(54) ACOUSTIC EMISSION SENSORS WITH INTEGRAL ACOUSTIC GENERATORS

(71) Applicant: Fisher Controls International LLC, Marshalltown, IA (US)

(72) Inventors: Bret Anthony Dahme, Marshalltown, IA (US); Paul Richard Kelly, Kennewick, WA (US); Curtis M. Nickolaus, Pasco, WA (US); Richard Allen Nordstrom, Marshalltown, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 0 days.

(21) Appl. No.: 15/333,658

(22) Filed: Oct. 25, 2016

(65) Prior Publication Data

US 2018/0113098 A1   Apr. 26, 2018

(51) Int. Cl.
   *G01N 29/14*   (2006.01)
   *G01N 29/30*   (2006.01)
   *G01N 29/28*   (2006.01)

(52) U.S. Cl.
   CPC ............ *G01N 29/30* (2013.01); *G01N 29/14* (2013.01); *G01N 29/28* (2013.01)

(58) Field of Classification Search
   CPC ........ G01N 29/14; G01N 29/30; G01N 29/28; G01N 29/4427; G01N 29/4436; G01H 3/005; G01V 13/00
   USPC ................. 73/587, 1.82, 590, 592, 593, 584
   See application file for complete search history.

(56) References Cited

U.S. PATENT DOCUMENTS

| 3,325,781 A | 6/1967 | Harris |
| 3,546,924 A | 12/1970 | Nussbaum et al. |
| 4,011,472 A * | 3/1977 | Feng .................. B06B 1/0625 310/328 |

(Continued)

FOREIGN PATENT DOCUMENTS

| DE | 10153297 | 4/2003 |
| DE | 202009014773 | 3/2011 |

(Continued)

OTHER PUBLICATIONS

International Searching Authority, "International Search Report and Written Opinion," issued in connection with PCT Application No. PCT/US2017/012904, dated May 10, 2017, 13 pages.

(Continued)

*Primary Examiner* — Manish S Shah
*Assistant Examiner* — Rose M Miller
(74) *Attorney, Agent, or Firm* — Hanley Flight & Zimmerman, LLC

(57) ABSTRACT

Example acoustic emission sensors with integral acoustic generators are disclosed. Example apparatus disclosed herein include an acoustic receiver, an acoustic generator, and a wear plate. The acoustic generator is disposed adjacent to the acoustic receiver. The wear plate is acoustically coupled to the acoustic receiver and to the acoustic generator. The wear plate is to convey acoustic energy from the acoustic generator to the acoustic receiver through a structure under test to which the apparatus is coupled. The wear plate includes first acoustic isolation to impede transmission of acoustic energy from the acoustic generator to the acoustic receiver through the wear plate.

20 Claims, 10 Drawing Sheets

(56) References Cited

U.S. PATENT DOCUMENTS

| | | | |
|---|---|---|---|
| 4,043,176 A * | 8/1977 | Graham | G01N 29/2437 73/1.82 |
| 4,043,180 A | 8/1977 | Morris et al. | |
| 4,437,332 A * | 3/1984 | Pittaro | G01B 17/02 73/1.82 |
| 4,519,251 A * | 5/1985 | Dickson | G01N 29/2493 73/639 |
| 4,567,770 A * | 2/1986 | Rumbold | G01N 29/28 73/617 |
| 4,922,754 A | 5/1990 | Horne et al. | |
| 5,005,415 A | 4/1991 | Holroyd | |
| 5,156,050 A | 10/1992 | Schmid et al. | |
| 5,435,168 A | 7/1995 | Granere | |
| 6,016,701 A * | 1/2000 | McClelland | G01N 29/041 73/620 |
| 6,672,131 B1 * | 1/2004 | Aldal | G01F 1/667 73/1.82 |
| 8,037,762 B2 | 10/2011 | La Rosa Flores et al. | |
| 8,311,759 B2 | 11/2012 | Sutherland | |
| 2001/0007203 A1 | 7/2001 | Goodman et al. | |
| 2005/0011278 A1 | 1/2005 | Brown et al. | |
| 2007/0034012 A1 | 2/2007 | Amir et al. | |
| 2010/0089161 A1 | 4/2010 | Taheri | |
| 2010/0218591 A1 | 9/2010 | Rhodes et al. | |
| 2017/0199161 A1 | 7/2017 | Nordstrom et al. | |
| 2017/0199162 A1 | 7/2017 | Nordstrom et al. | |

FOREIGN PATENT DOCUMENTS

| | | |
|---|---|---|
| EP | 0727259 | 8/1996 |
| WO | 2011050992 | 5/2011 |

OTHER PUBLICATIONS

United States Patent and Trademark Office, "Non-Final Office Action," issued in connection with U.S. Appl. No. 15/387,341, dated Jan. 19. 2018, 15 pages.

United States Patent and Trademark Office, "Non-Final Office Action," issued in connection with U.S. Appl. No. 14/992,755, dated Jan. 18, 2018, 15 pages.

International Searching Authority, "International Search Report and Written Opinion," issued in connection with International Patent Application No. PCT/US2017/057957, dated Jan. 26, 2018, 13 pages.

* cited by examiner

ACOUSTIC EMISSION SENSORS WITH INTEGRAL ACOUSTIC GENERATORS

FIELD OF THE DISCLOSURE

This disclosure relates generally to nondestructive testing and, more particularly, to acoustic emission sensors with integral acoustic generators.

BACKGROUND

In recent years, acoustic emission testing has been used to measure how much a structure can be loaded before developing a crack, detecting cracks in structures, and detecting internal leaks in fluid-carrying equipment (e.g., valves). During acoustic emission testing, a structure undergoing testing is gradually loaded to known stresses (typically greater than a service stress the structure will experience in actual use) and acoustic emission sensors are used to detect cracks as they occur in the loaded structure (e.g., sizes and locations of the cracks). In other cases, a valve is monitored with an acoustic emission sensor to detect internal leaks as they occur within the valve. Acoustic emission sensors typically include a receiver coupled to a wear plate, connected to a computer via a data cable, and covered by a housing. The receiver typically includes a piezoelectric element or transducer. The wear plate typically acts as an interface (e.g., a shield) between the receiver and the structure undergoing testing. When an acoustic emission resulting from a structural change (e.g., production of a crack, production of an internal valve leak, etc.) arrives at the receiver, the piezoelectric transducer produces an electrical signal that is transmitted to the computer via the data cable.

However, acoustic emissions resulting from cracks are not repeatable (e.g., only one crack and one respective acoustic emission occur for a given test load). Therefore, the acoustic emission sensor must detect the acoustic emission at the singular occurrence when the structural change first develops to collect precise data for the structure undergoing acoustic emission testing. Further, while internal leaks continuously produce acoustic emissions, the acoustic emission sensor must precisely detect the acoustic emissions to determine the severity of the internal leak. Precise acoustic emission sensing is highly dependent on a good (e.g., acoustically transmissive) bond between the wear plate and the tested structure.

To ensure a good bond between the tested structure and the wear plate, a fluid (e.g., glue, grease) is typically used between the structure and the wear plate to fill voids (typically microscopic) between the wear plate and the structure that would otherwise impede acoustic transmission from the structure to the acoustic emission sensor. Further, the bond is tested for acoustic transmissibility by applying a test acoustic signal of a known intensity to the structure. Reception of the test signal by the receiver at or near the initial intensity is indicative of a good bond.

SUMMARY

In one example, an apparatus includes an acoustic receiver; an acoustic generator and a wear plate. The acoustic generator is disposed adjacent to the acoustic receiver. The wear plate is acoustically coupled to the acoustic receiver and to the acoustic generator. The wear plate is to convey acoustic energy from the acoustic generator to the acoustic receiver through a structure under test to which the apparatus is coupled. The wear plate includes first acoustic isolation to impede transmission of acoustic energy from the acoustic generator to the acoustic receiver through the wear plate.

In another example, an apparatus includes an acoustic generator, a receiver, and a wear plate. The receiver is disposed adjacent to the acoustic generator. The wear plate is acoustically coupled to the acoustic generator and to the receiver. The wear plate is to convey acoustic energy from the acoustic generator to a structure under test and to the receiver.

In another example, an apparatus includes a housing, a receiver portion of a wear plate, an acoustic receiver, an acoustic signal generating element, an acoustic generator portion of the wear plate, and an adhesive polymer. The receiver portion of the wear plate is supported by the housing. The acoustic receiver is acoustically coupled to the receiver portion and is disposed in the housing. The acoustic signal generating element is disposed in the housing. The acoustic generator portion of the wear plate is acoustically coupled to the acoustic signal generating element. The adhesive polymer is sandwiched between the acoustic generator portion and the receiver portion and is to impede acoustic energy transmission from the acoustic generator portion to the receiver portion.

Figure 1:
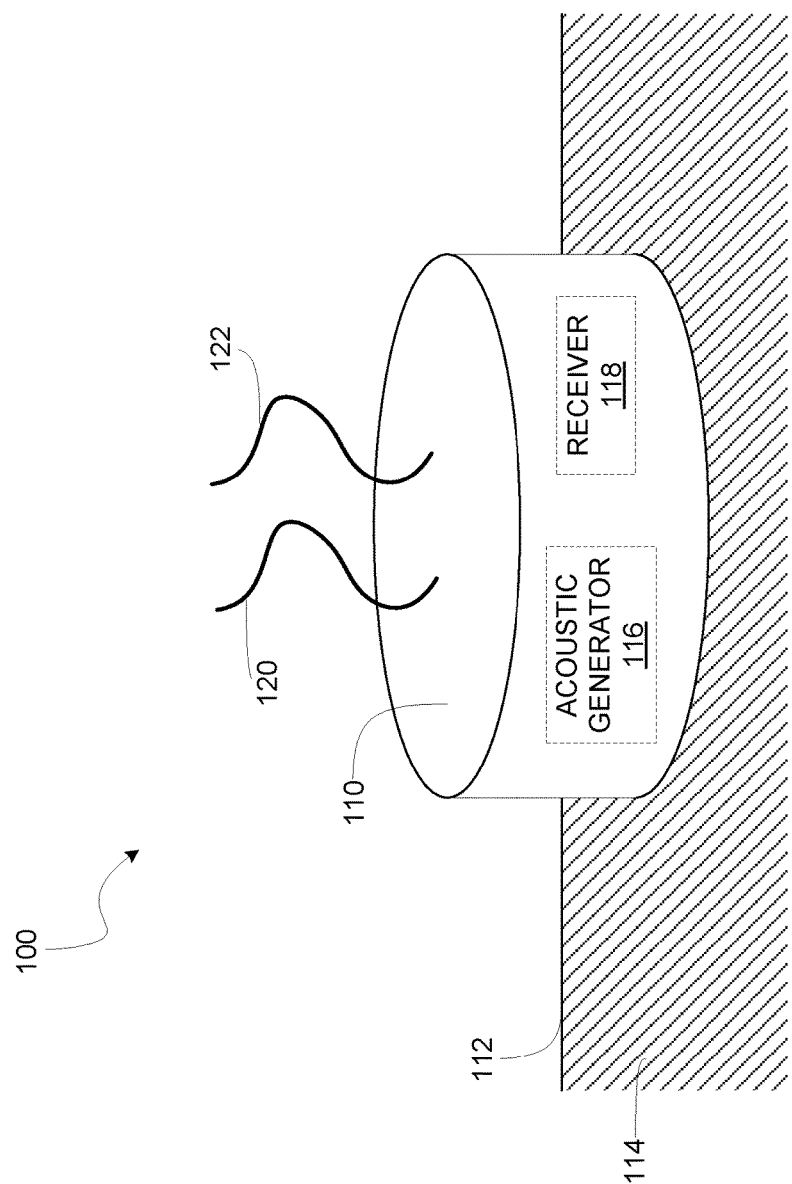
FIG. 1 illustrates an example acoustic emission sensor apparatus implemented with an example acoustic generator described herein.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

When using a conventional acoustic emission sensor, variables with respect to the intensity of a test acoustic signal may arise because the acoustic generator that provides the test acoustic signal is physically separate from the acoustic emission sensor and thus requires its own acoustically transmissive mounting. If a highly degraded test acoustic signal is received by the receiver, it is unclear whether the mounting of the acoustic generator, the mounting of the acoustic emission sensor, or both are poor. Further, where the acoustic generator and/or acoustic emission sensor are temporarily mounted on a structure, accurately replicating a testing arrangement of the acoustic generator and the acoustic emission sensor for follow-up acoustic emission testing is often difficult. Further, some structures do not have adequate surface area on which an acoustic generator and a separate acoustic emission sensor may be mounted.

FIG. 1 illustrates an example acoustic emission sensor apparatus 100 implemented with an example acoustic generator described herein. More specifically, FIG. 1 shows an acoustic emission sensor assembly 110 constructed in accordance with the teachings herein mounted to a surface 112 of a structure 114 to be tested and/or monitored. The acoustic emission sensor assembly 110 includes an acoustic generator 116, a receiver 118, an acoustic generator cable 120, and a receiver cable 122. In some examples, the acoustic generator cable 120 provides electrical power to the acoustic generator 116. In some examples, the receiver cable 122 carries electrical signals (e.g., voltages, currents, digital data, etc.) from the receiver 118 to a computer or other processing device (not shown in FIG. 1). In some examples, the acoustic generator 116 provides acoustic signals of any duration (e.g., the acoustic generator 116 is an acoustic signal generator), as will be explained below in conjunction with FIGS. 2-8. The acoustic generator 116 may facilitate testing of the mounting (e.g., acoustic coupling) of the acoustic emission sensor assembly 110 to the structure 114, as will be explained in greater detail below in conjunction with FIGS. 2-8.

Figure 2:
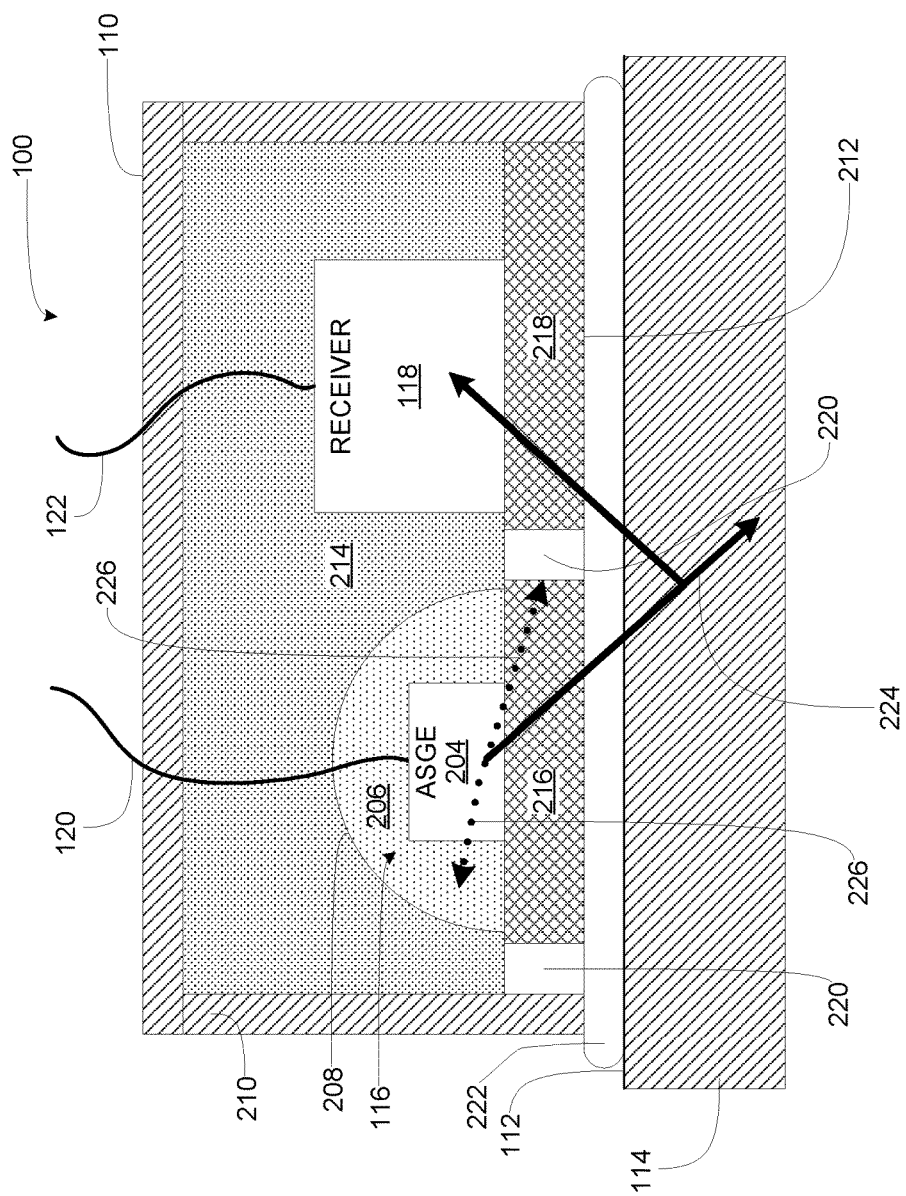
FIG. 2 is a cross-sectional view of an example arrangement of the example acoustic emission sensor apparatus of FIG. 1.

FIG. 2 is a cross-sectional view of an example arrangement of the example acoustic emission sensor apparatus 100 of FIG. 1. In the illustrated example of FIG. 2, the acoustic generator 116 further includes an acoustic signal generating element ("ASGE") 204 and an acoustic isolation material, or more generally, an isolator 206. The acoustic signal generating element 204 may be any type of acoustic signal-generating device (e.g., an asymmetric weight buzzer motor, a piezoelectric crystal, etc.). In some examples, the acoustic signal generating element 204 produces relatively brief acoustic signals (e.g., pulses). In some examples, the acoustic signal generating element 204 produces substantially continuous acoustic signals (e.g., vibration). In some examples, the isolator 206 is hemispherically shaped and receives the acoustic signal generating element 204. In some examples, the isolator 206 is composed of a material with high acoustic impedance (e.g., cork, sponge, foam, rubber, etc.). In some examples, the isolator 206 is a vacuum and has an airtight outer skin 208 to maintain the vacuum. Additionally, in the illustrated example of FIG. 2, the acoustic emission sensor assembly 110 further includes a housing 210 and a wear plate 212. In some examples, the acoustic generator 116 and the receiver 118 are disposed in the housing 210. For example, the housing 210 is external to (e.g., contains) and protects the acoustic generator 116 and the receiver 118 from potential damage during mounting and/or handling. In some examples, the housing 210 supports the wear plate 212. In some examples, the housing 210 is backfilled with fixative 214 (e.g., thermoplastic potting, etc.) that retains and partially encapsulates the acoustic generator 116 and the receiver 118. In some examples, the fixative 214 encapsulates and receives the isolator 206 of the acoustic generator 116. In some examples, the wear plate 212 includes an acoustic generator portion 216 joined to a receiver portion 218 by an adhesive polymer 220. The adhesive polymer 220 impedes acoustic transmission between the acoustic generator portion 216 and the receiver portion 218. In some examples, the acoustic signal generating element 204 of the acoustic generator 116 and the isolator 206 of the acoustic generator 116 are in acoustic communication with the acoustic generator portion 216 of the wear plate 212. Accordingly, the isolator 206 impedes acoustic transmission (e.g., isolates) from the acoustic signal generating element 204 to the fixative 214. In some examples, the receiver 118 is operatively associated and in acoustic communication with the receiver portion 218 of the wear plate 212. In some examples, the adhesive polymer 220 surrounds the acoustic generator portion 216 of the wear plate 212. In the example of FIG. 2, the adhesive polymer 220 joins the acoustic generator portion 216 to the housing 210. In some examples, as explained in greater detail below with aid of FIG. 6, the acoustic generator portion 216 is surrounded by the receiver portion 218. Typically, a fluid 222 is sandwiched or otherwise disposed between the wear plate 212 and the surface 112 when mounting the acoustic emission sensor assembly 110 to the structure 114. In some examples, the fluid 222 is viscous (e.g., grease, caulk, petroleum jelly, etc.). In some examples, particularly where the acoustic emission sensor assembly 110 is to be permanently mounted, the fluid 222 is an adhesive (e.g., epoxy, glue, paste, cement, etc.). In some examples, the acoustic emission sensor assembly 110 is mechanically fastened to structure 114 (e.g., screwed, clamped, bolted, etc.) (not shown in FIG. 2). In some examples, the acoustic emission sensor assembly 110 is magnetically held to the structure 114 (not shown in FIG. 2). In the example of FIG. 2, the acoustic emission sensor assembly 110 is adhered to the structure via the fluid 222.

In operation, the acoustic signal generating element 204 generates a test acoustic signal that may result in a transmitted signal 224 and blocked signals 226. The transmitted signal 224 travels from the acoustic signal generating element 204, through the acoustic generator portion 216 of the wear plate 212, through the fluid 222, and into the structure 114. Further, portions of the transmitted signal 224 are attenuated (e.g., lost, absorbed, etc.) by the structure 114 while other portions of the transmitted signal 224 return from the structure 114, through the fluid 222, through the receiver portion 218 of the wear plate 212, and into the receiver 118. In contrast, the adhesive polymer 220 prevents (e.g., blocks, shields, impedes) the blocked signals 226 from traveling through the wear plate 212 directly to the receiver 118. Further, the isolator 206 prevents the blocked signals 226 from traveling through the fixative 214 directly to the receiver. Accordingly, the receiver 118 receives test acoustic signals that have traveled through the structure 114 (e.g., the transmitted signal 224) and does not receive test acoustic signals that would otherwise bypass the structure 114 (e.g., the blocked signals 226). In other words, the adhesive polymer 220 and the isolator 206 impede reception of false positives by the receiver 118. Thus, the quality of the mounting and acoustic coupling of the acoustic emission sensor assembly 110 to the structure 114 can be tested. In some examples, where the transmitted signal 224 is received by the receiver 118 with a predictable amplitude of approximately the same intensity (e.g., about 90% or more) as transmitted by the acoustic signal generating element 204, the acoustic emission sensor assembly 110 is well mounted. In some examples, where the intensity of the transmitted signal 224 as received by the receiver 118 is degraded from its intensity as transmitted by the acoustic signal generating element 204 or the transmitted signal 224 is not received by the receiver 118, the acoustic emission sensor assembly 110 is poorly mounted. Accordingly, in some examples, the isolator 206 prevents portions of test signals (e.g., blocked signals 226) from traveling through the fixative 214 while allowing the acoustic signal generating element 204 to transmit further portions of test signals (e.g., transmitted signal 224) through the acoustic generator portion 216 of the wear plate 212. Thus, in some examples, the quality of the mounting is directly related to the intensity of the transmitted signal 224 as received by the receiver 118. Further arrangements of the isolator 206 are described below in conjunction with FIGS. 3-5.

Figure 3:
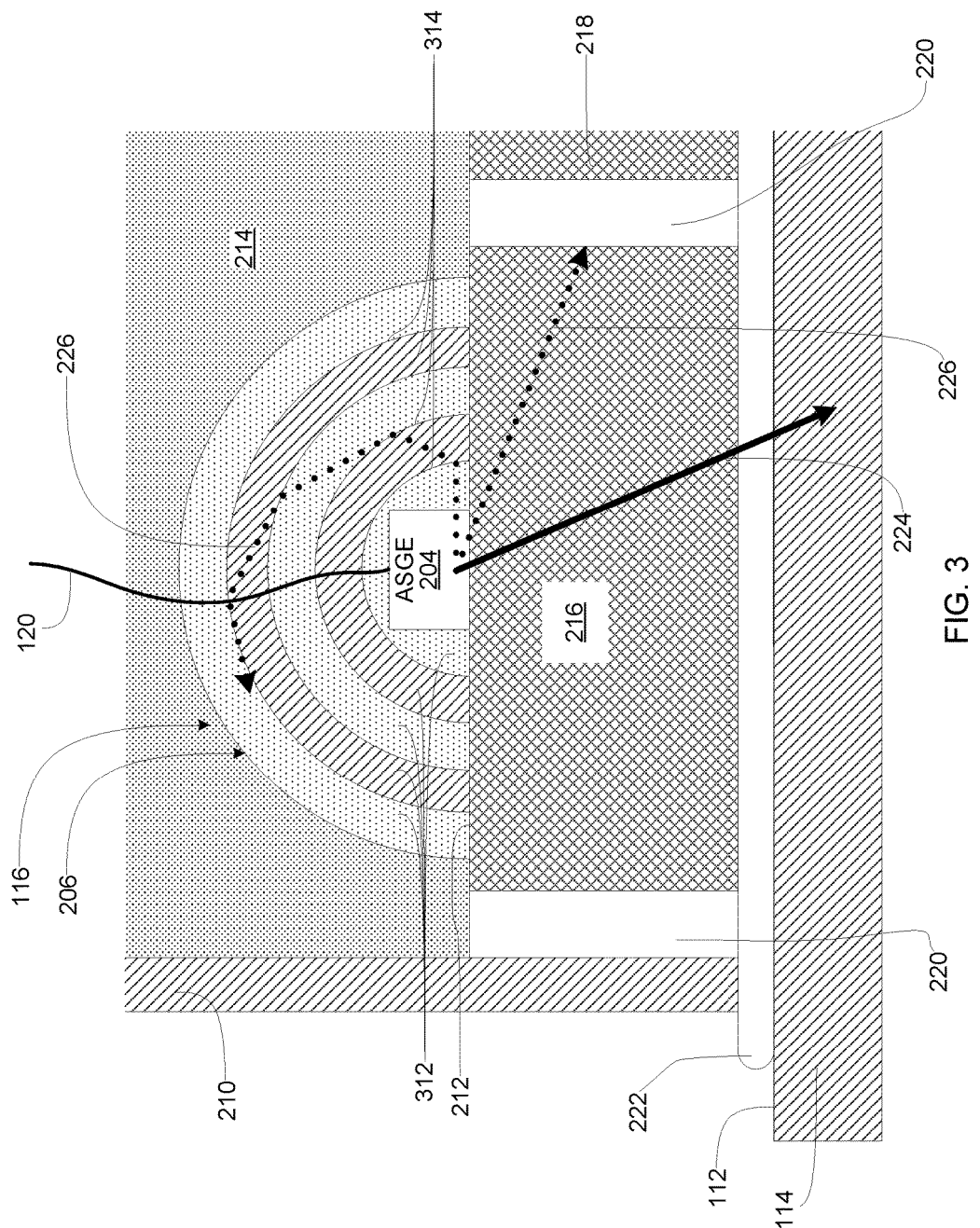
FIG. 3 is an enlarged cross-sectional view of an alternative example arrangement of the example acoustic generator of FIG. 2.

FIG. 3 is an enlarged cross-sectional view of an alternative example arrangement of the example acoustic generator 116 of FIGS. 1 and 2. In the illustrated example of FIG. 3, the isolator 206 includes multiple isolation layers 312. In some examples, the isolation layers 312 are alternating layers of high acoustic impedance material, discussed above, and low acoustic impedance material (e.g., metals, etc.). Thus, in some examples, the isolation layers 312 are high and low acoustic impedance layers. However, the isolator 206 can be any combination of materials to achieve a desirable acoustic impedance.

In operation, as an acoustic test signal (e.g., the blocked signal 226) reaches boundaries 314 between the isolation layers 312, the test signal is refracted according to Snell's law, shown below, where $n_1$ is the acoustic refractive index of the material from which the test signal is coming, $\Theta_1$ is the angle away from normal (e.g., perpendicular) at which the test signal approaches the boundary 314, $n_2$ is the acoustic refractive index of the material into which the test signal is entering, $\Theta_2$ is the angle away from normal at which the test signal crosses the boundary 314.

$$n_1 \sin \Theta_1 = n_2 \sin \Theta_2$$

In some examples, due to the refraction of the test signal at the boundaries 314 between the hemispherical isolation layers 312, the test signal becomes trapped in the isolator 206, as exemplified by the curled blocked signal 226. Thus, in some examples, the isolation layers 312 prevent test signals from reaching and/or traveling through the fixative 214. Further arrangements of the isolator 206 are described below in conjunction with FIGS. 4-5.

Figure 4:
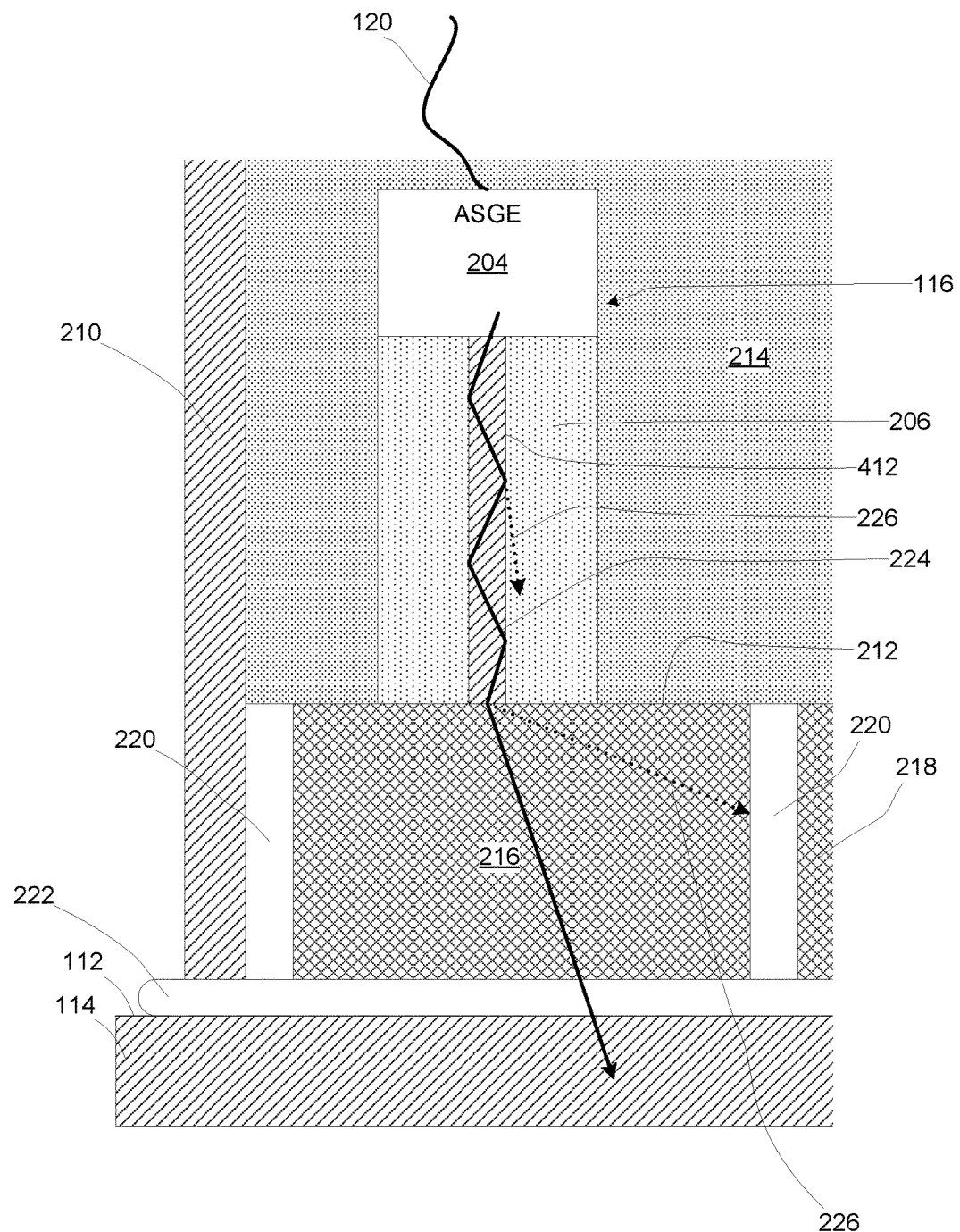
FIG. 4 is an enlarged cross-sectional view of an alternative example arrangement of the example acoustic generator of FIG. 2.

FIG. 4 is an enlarged cross-sectional view of an alternative example arrangement of the example acoustic generator 116 of FIGS. 1 and 2. In the illustrated example of FIG. 4, the acoustic generator 116 further includes a waveguide rod 412. In some examples, the waveguide rod 412 is composed of a low acoustic impedance material. In some examples, the waveguide rod 412 is perpendicular to the acoustic generator portion 216, as shown in FIG. 4. In some examples, the waveguide rod 412 is disposed at a non-perpendicular angle to the acoustic generator portion 216 (not pictured in FIG. 4). In some examples, the isolator 206 surrounds the waveguide rod 412. Further, in some examples, the acoustic signal generating element 204 is attached to the acoustic generator portion 216 of the wear plate 212 via the isolator 206 and the waveguide rod 412. In some such examples, the waveguide rod 412 acoustically couples the acoustic signal generating element 204 to the acoustic generator portion 216. In some such examples, the isolator 206 and the waveguide rod 412 act as an intermediary (e.g., a spacer, a standoff, an insert, etc.) between the acoustic signal generating element 204 and the acoustic generator portion 216 of the wear plate 212. In operation, the waveguide rod 412 directs a test signal (e.g., the transmitted signal 224) away from the acoustic signal generating element 204 and into the acoustic generator portion 216 of the wear plate 212. In some examples, the transmitted signal 224 is refracted according to Snell's law, described above, when traversing from the waveguide rod 412 to the acoustic generator portion 216. Further, in operation, in some examples, the transmitted signal 224 is refracted according to Snell's law when crossing from the acoustic generator portion 216 to the structure 114. Thus, in some examples, the angle between the waveguide rod 412 and acoustic generator portion 216 controls the approach of the transmitted signal 224 into the acoustic generator portion 216 and into the structure 114. Further, in operation, the isolator 206 prevents portions of the test signal that diffuse away from the waveguide rod 412 from reaching the fixative 214, as exemplified by one of the blocked signals 226. Further arrangements of the isolator 206 are described below in conjunction with FIG. 5

Figure 5:
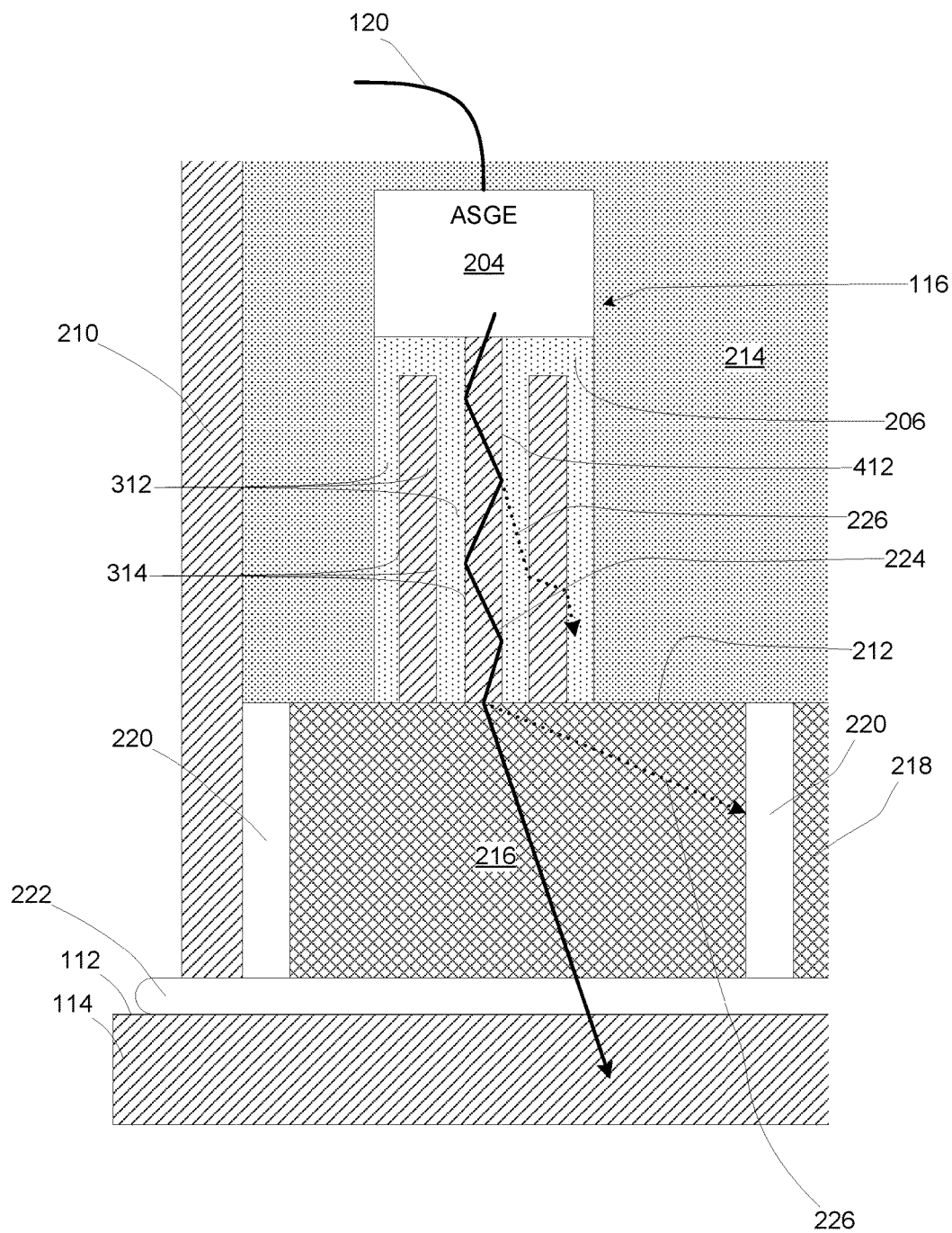
FIG. 5 is an enlarged cross-sectional view of an alternative example arrangement of the example acoustic generator of FIG. 4.

FIG. 5 is an enlarged cross-sectional view of an alternative example arrangement of the example acoustic generator 116 of FIG. 4. In the illustrated example of FIG. 5, similar to FIG. 3, the isolator 206 includes the isolation layers 312. Similar to FIG. 3, discussed above, in some examples, the isolation layers 312 are alternating layers of high acoustic impedance material and low acoustic impedance material. In some examples, as shown in FIG. 5, the isolation layers are cylindrically shaped and are alternately stacked radially away from the waveguide rod 412. In operation, as a portion of a test signal that has diffused away from the waveguide rod 412 reaches boundaries 314 between the isolation layers 312, the test signal is refracted according to Snell's law, as discussed above and exemplified by the zigzag blocked signal 226. In some examples, due to the refraction of the diffused test signal at the boundaries 314 between the radially alternating isolation layers 312, the path length of the diffused test signal is increased. In some examples, the intensity of the diffused test signal is dissipated along this increased path length before reaching the fixative 214. Thus, in some examples, the isolation layers 312 prevent test signals from reaching and/or traveling through the fixative 214. However, in some examples, due to Snell's law, the test signal is reflected completely at the boundary 314 between the waveguide rod 412 and the isolator 206, as exemplified by the transmitted signal 224. Thus, in some examples, the isolator 206 prevents test signals from exiting the waveguide rod 412 before reaching the acoustic generator portion 216 of the wear plate 212. Arrangements of the wear plate 212 are explained below in conjunction with FIGS. 6-7.

Figure 6:
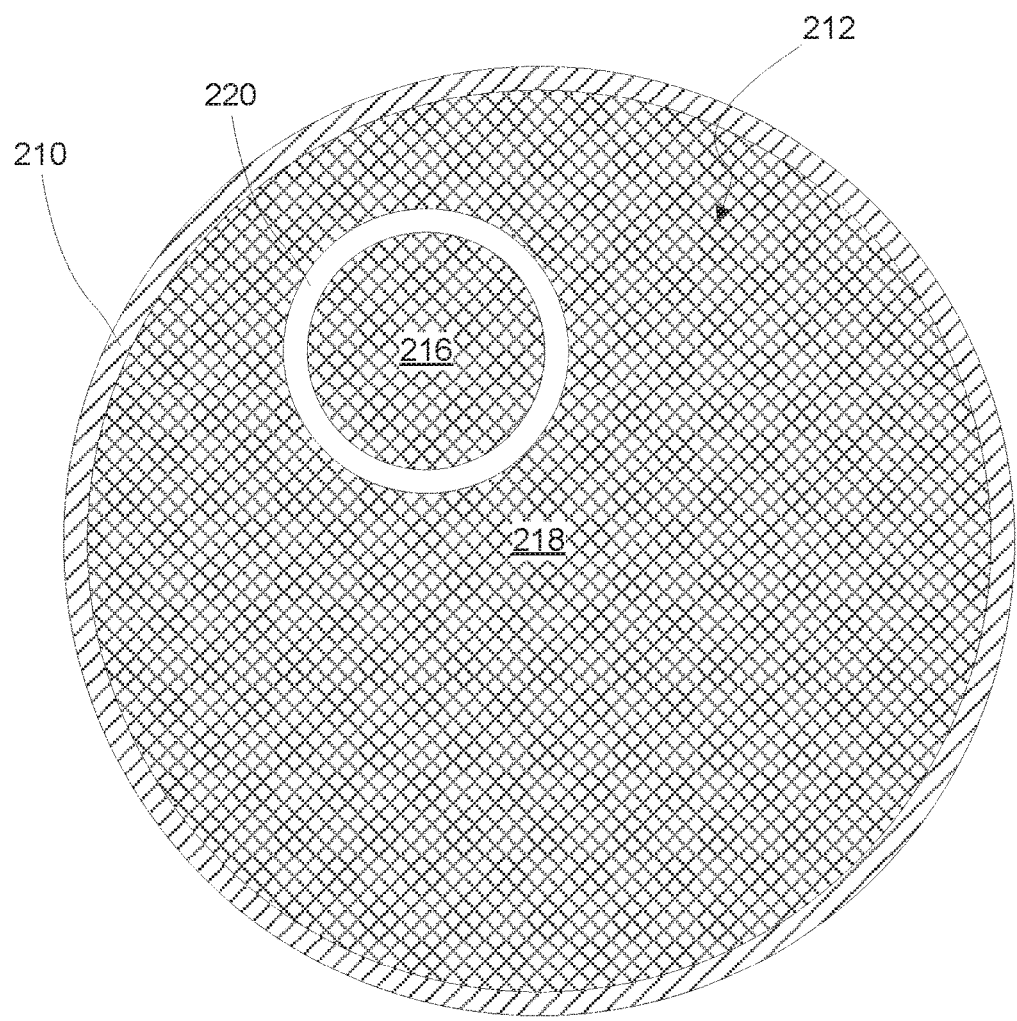
FIG. 6 is a bottom view of the example acoustic emission sensor of FIG. 1 implemented with an example wear plate described herein.

FIG. 6 is a bottom view of the example acoustic emission sensor assembly 110 of FIG. 1 implemented with an example wear plate 212 described herein. In the illustrated example of FIG. 6, the housing 210 and the wear plate 212 are generally circular. In some examples, the housing 210 is joined to the wear plate 212. Further, in some examples, the acoustic generator portion 216 of the wear plate 212 is formed as an island (e.g., a cutout, a removed portion, etc.)

and surrounded by the adhesive polymer 220, which is in turn surrounded by the receiver portion 218. Thus, the acoustic generator portion 216 is acoustically isolated from the receiver portion 218 by the adhesive polymer 220. In the example of FIG. 6, the acoustic generator portion 216 is shown as circular. However, other shapes may be used. In some examples, the receiver portion 218 has a greater surface area than the acoustic generator portion 216.

Figure 7:
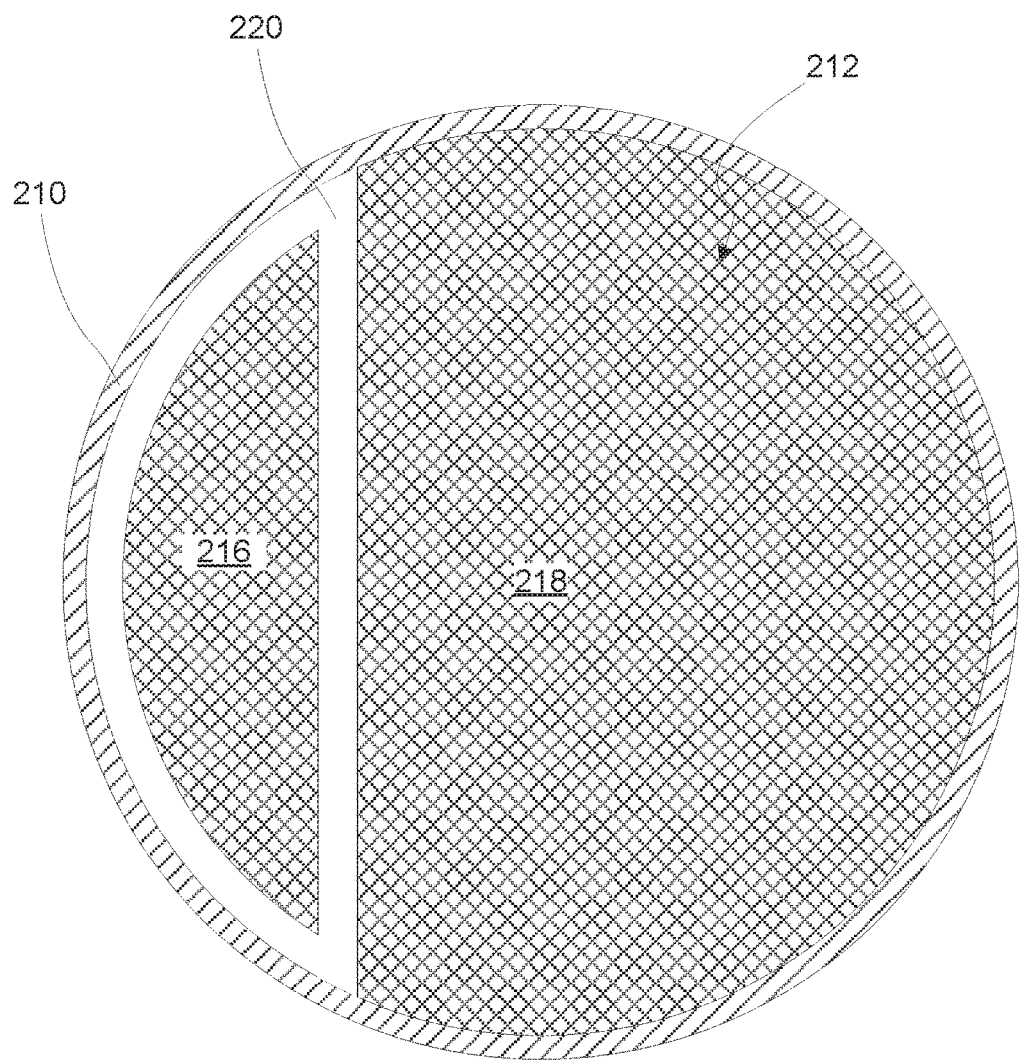
FIG. 7 is a bottom view of the example acoustic emission sensor of FIG. 1 implemented with an alternative example arrangement of the example wear plate described herein.

FIG. 7 is a bottom view of the example acoustic emission sensor assembly 110 of FIG. 1 implemented with an alternative example arrangement of the example wear plate 212 described herein. In the illustrated example of FIG. 7, the housing 210 and the wear plate 212 are generally circular, although other shapes are possible. In some examples, the adhesive polymer 220 is joined to the housing 210 and to the receiver portion 218 to surround the acoustic generator portion 216. Thus, in some such examples, where the wear plate 212 is generally circular, the acoustic generator portion 216 and the receiver portion 218 are crescent-shaped. Thus, the acoustic generator portion 216 is acoustically isolated from the receiver portion 218 and from the housing 210 by the adhesive polymer 220.

Figure 8:
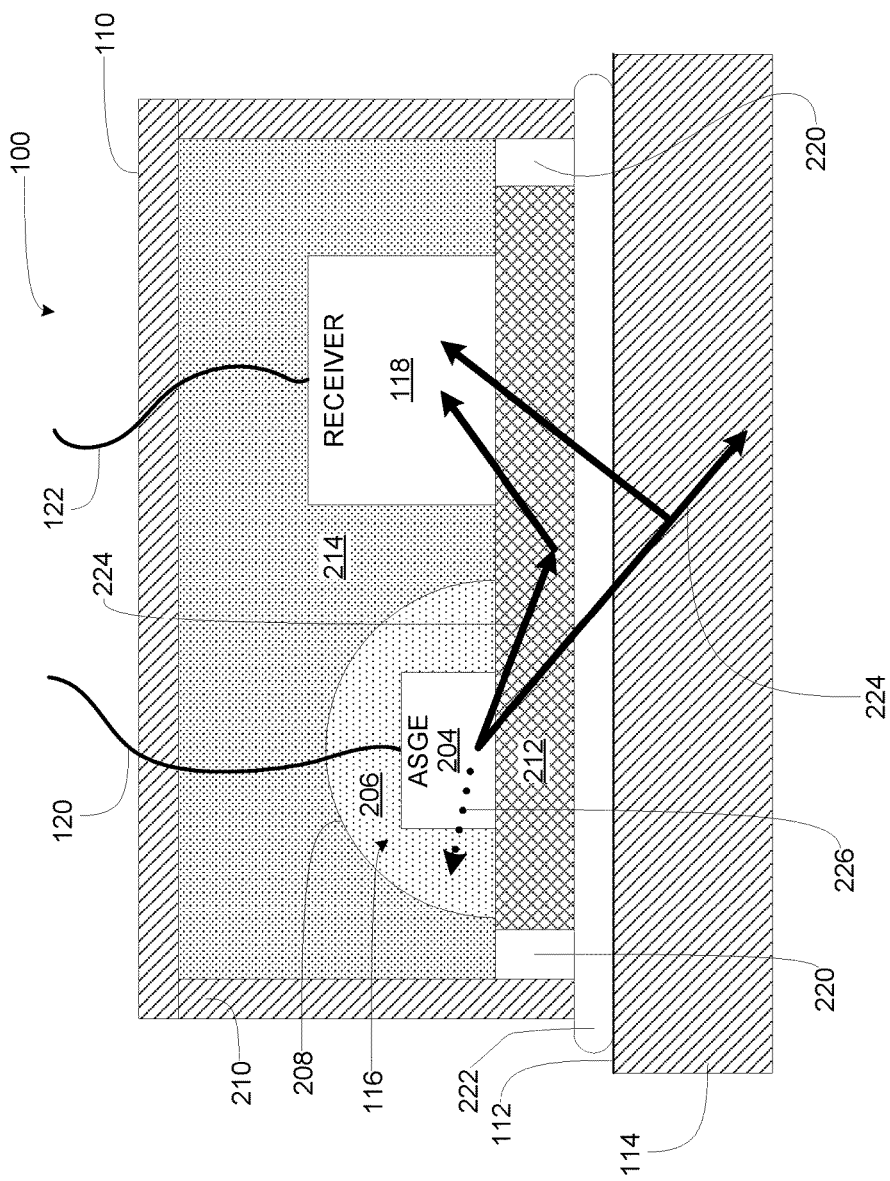
FIG. 8 is a cross-sectional view of an alternative example arrangement of the example acoustic emission sensor apparatus of FIG. 1.

FIG. 8 is a cross-sectional view of an alternative example arrangement of the example acoustic emission sensor apparatus 100 of FIG. 1. In the illustrated example of FIG. 8, the wear plate 212 is unitary. In some examples, the acoustic signal generating element 204 and the receiver 118 are acoustically linked via the wear plate 212. In some examples, the wear plate 212 is acoustically isolated from the housing 210 by the adhesive polymer 220.

In operation, in some examples, prior to mounting the acoustic emission sensor assembly 110 to the structure 114, the acoustic signal generating element 204 generates a test acoustic signal that travels directly to the receiver 118 via the wear plate 212. In some such examples, the test acoustic signal as received by the receiver 118 is a benchmark test acoustic signal (e.g., a known acoustic intensity). Further, in operation, in some examples, after mounting the acoustic emission sensor assembly 110 to the structure 114, the acoustic signal generating element 204 generates a further test acoustic signal that results in the transmitted signals 224 and the blocked signal 226. In some examples, as the transmitted signals 224 diffuse away from the acoustic signal generating element 204, portions of the transmitted signals 224 travel through the wear plate 212 to the receiver 118, other portions of the transmitted signals 224 return to the receiver 118 via the structure 114, and further portions of the transmitted signals 224 are attenuated (e.g., lost, absorbed, etc.) by the structure 114. Thus, because the transmitted signals 224 radiate into all possible paths, as the quality of the mounting between the wear plate 212 and the structure 114 improves (e.g., the acoustic transmissivity increases), the portion of the transmitted signals 224 attenuated by the structure 114 increases and the combined energy of the transmitted signals 224 received by the receiver 118 decreases, and vice-versa. For example, where the acoustic emission sensor assembly 110 is poorly mounted, the transmitted signals 224 are acoustically impeded from crossing from the wear plate 212 into the structure 114. For example, in contrast, where the acoustic emission sensor assembly 110 is well mounted, the transmitted signals 224 are not acoustically impeded from crossing from the wear plate 212 into the structure 114. Thus, by comparing the intensity (e.g., the combined portions) of the transmitted signals 224 received by the receiver 118, the quality of the mounting and the acoustic coupling of the acoustic emission sensor assembly 110 to the structure 114 can be tested. In some examples, where the intensity of the transmitted signals 224 as received by the receiver 118 is degraded as compared to the benchmark (e.g., the transmitted signals 224 are received by the receiver 118 with an amplitude of approximately 10% or less of the benchmark), the acoustic emission sensor assembly 110 is well mounted. In some such examples, a relatively large portion of the transmitted signals 224 have traveled into and have been attenuated by the structure 114. Further, in some examples, where the intensity of the transmitted signals 224 as received by the receiver 118 approximately matches the benchmark (e.g., the transmitted signals 224 are received by the receiver 118 with a predictable amplitude of approximately 90% or more of the benchmark), the acoustic emission sensor assembly 110 is poorly mounted. In some such examples, a relatively large portion of the transmitted signals 224 have not traveled into and have not been attenuated by the structure 114). Thus, in some examples, the quality of the mounting is inversely related to the intensity of the transmitted signals 224 as received by the receiver 118.

Figure 9:
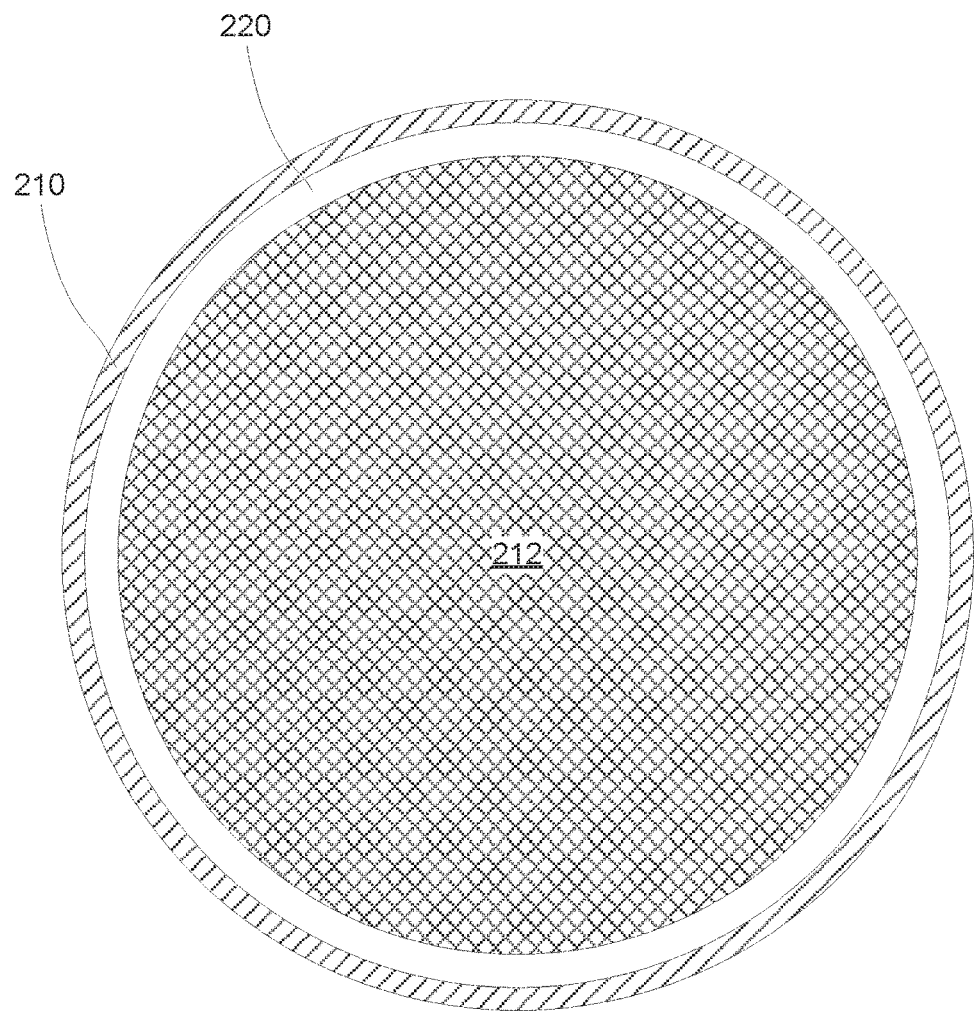
FIG. 9 is a bottom view of the example acoustic emission sensor of FIG. 1 implemented with an alternative example arrangement of the example wear plate described herein.

FIG. 9 is a bottom view of the example acoustic emission sensor of FIG. 1 implemented with an alternative example arrangement of the example wear plate described herein. In the illustrated example of FIG. 9, the adhesive polymer 220 is joined to the housing 210 and to the wear plate 212 to surround the wear plate 212. Thus, in some such examples, the wear plate 212 is an island. Thus, the wear plate 212 is acoustically isolated from the housing 210 by the adhesive polymer 220.

Figure 10:
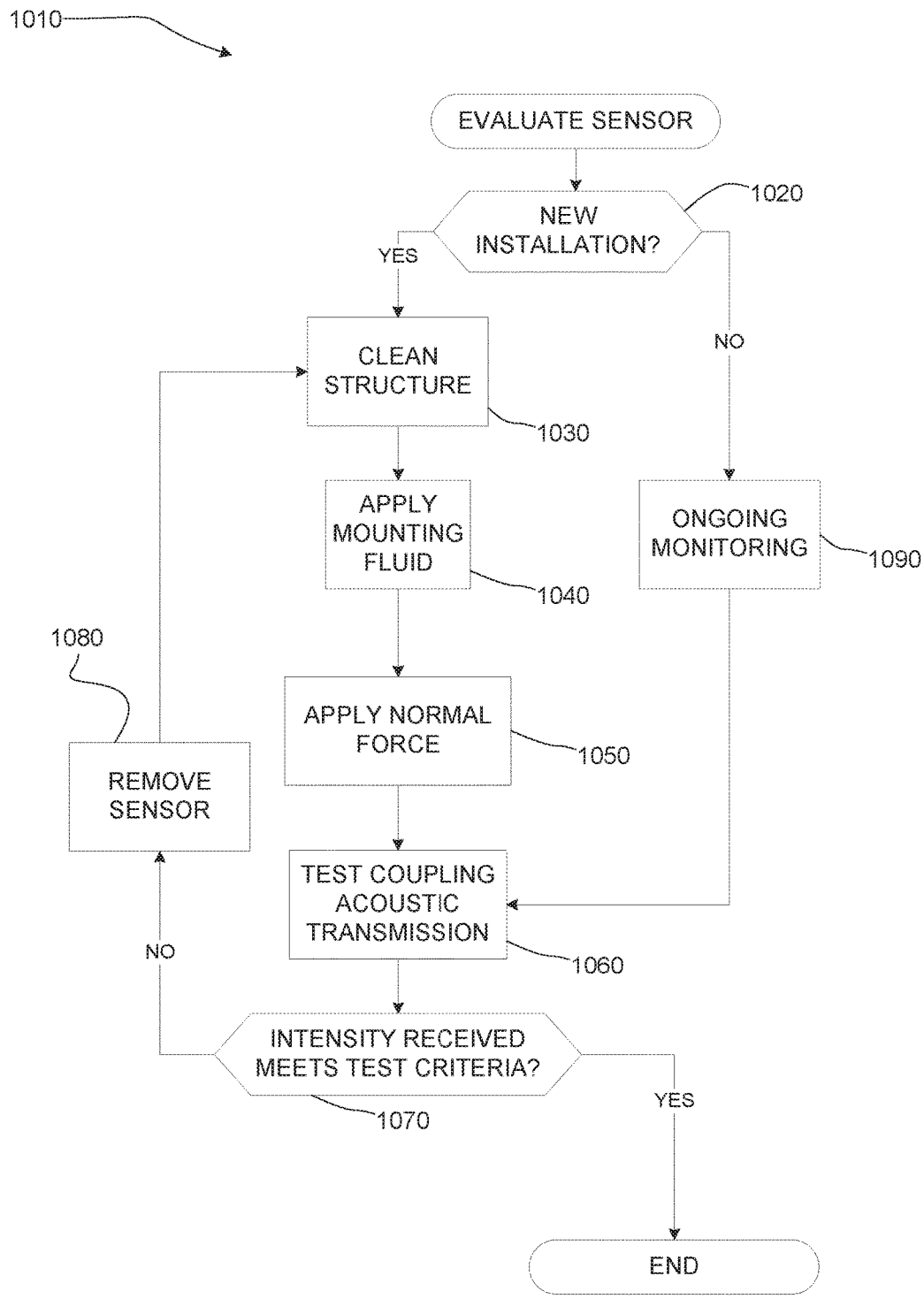
FIG. 10 is a flowchart representative of an example method that may be performed to mount the example acoustic emission sensor apparatus of FIGS. 1-9.

A flowchart representative of an example method to mount the example acoustic emission sensor assembly 110 of FIGS. 1-9 is shown in FIG. 10. In some examples, where the example method is implemented using machine readable instructions, the machine readable instructions comprise a program for execution by a processor. The program may be embodied in software stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example method is described with reference to the flowchart illustrated in FIG. 10, many other methods of implementing the example acoustic emission sensor assembly 110 may alternatively be used. For example, the order of execution of the blocks may be changed, and/or some of the blocks described may be changed, eliminated, or combined.

As mentioned above, the example method of FIG. 10 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example methods of FIG. 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 is a flowchart representative of an example method 1010 that may be executed to implement the example acoustic emission sensor assembly 110 of FIGS. 1-9. The example method 1010 may be performed, for example, to evaluate the mounting quality of an acoustic emission sensor assembly to a structure to be tested, monitored, and/or undergoing monitoring with acoustic emission testing.

To begin, a determination is made whether the acoustic emission sensor to be mounting quality tested is part of a new installation (block 1020). If the acoustic emission sensor to be tested is part of a new installation (block 1020), a structure to be tested and/or monitored with acoustic emission testing is cleaned to remove particulate and/or surface residues that may impede acoustic transmission between the structure (e.g., the structure 114) and an acoustic emission sensor assembly (e.g., the acoustic emission sensor assembly 110) (block 1030). Next, a mounting fluid (e.g., the fluid 222) is applied to the structure and/or the acoustic emission sensor assembly (block 1040). In some instances, the mounting fluid is a viscous fluid (e.g., grease, caulk, petroleum jelly, etc.). In some instances where the structure is to undergo long-term testing and/or monitoring, the mounting fluid is an adhesive (e.g., glue, epoxy, cement, paste, etc.). Further, a normal (e.g., approximately perpendicular) force, with respect to a surface of the structure, is applied to the acoustic emission sensor assembly to couple the acoustic emission sensor assembly to the structure by sandwiching and spreading the mounting fluid between the structure and a wear plate (e.g., the wear plate 212) of the acoustic emission sensor assembly (block 1050). In some examples, the mounting fluid is sandwiched to be spread to an approximately uniform thickness. Then, the acoustic transmissibility of the mount is tested by sending an acoustic test signal from an acoustic generator (e.g., the acoustic generator 116) and receiving the test signal with a receiver (e.g., the receiver 118) (block 1060). In some examples, the test signal travels from the acoustic generator through an acoustic generator portion (e.g., the acoustic generator portion 216) of the wear plate, through the mounting fluid, into the structure and returns from the structure through the mounting fluid and through a receiver portion (e.g., the receiver portion 218) of the wear plate to the receiver (block 1060). In some examples, via the wear plate, a portion of the test signal travels from the acoustic generator to the receiver while another portion travels from the acoustic generator to the structure. If the intensity of the test signal as received is within desired test criteria (e.g., about 90% or greater of the intensity of the originally transmitted signal, degraded as compared to a benchmark test signal, etc.) (block 1070), then the acoustic emission sensor assembly is well-mounted to the structure and the method ends. If the intensity of the signal as received is not within the test criteria (block 1070), then the acoustic emission sensor is poorly mounted, the acoustic emission sensor is removed (block 1080), and the method returns to the cleaning step of block 1030.

If the acoustic emission sensor to be tested is not part of a new installation (block 1020), then the acoustic emission sensor is part of an ongoing monitoring plan (block 1090) and the method progresses to the testing step of block 1060.

From the foregoing, it will be appreciated that the above disclosed methods, apparatus and articles of manufacture may provide acoustic emission sensor assemblies that can be confidently mounted (e.g., the sensor will collect precise data) to structures to be tested and/or monitored via acoustic emissions. Additionally, the acoustic emission sensor assemblies disclosed may permit follow-up mounting quality testing without the need to mount separate test acoustic generators, which may be particularly beneficial where the structure is undergoing long-term or permanent acoustic emission testing. Furthermore, the number of mountings involved in acoustic emission testing may be halved utilizing the acoustic emission sensor assembly with an integral test acoustic generator described herein, thus simplifying and accelerating acoustic emission testing processes.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
an acoustic receiver disposed in a housing;
an acoustic generator disposed in the housing adjacent to the acoustic receiver, the acoustic generator including an isolator;
a fixative disposed in the housing to at least partially encapsulate the acoustic receiver and the acoustic generator, the isolator to impede transmission of acoustic energy from the acoustic generator into the fixative within the housing; and
a wear plate acoustically coupled to the acoustic receiver and to the acoustic generator, wherein the wear plate is to convey acoustic energy from the acoustic generator to the acoustic receiver through a structure under test to which the wear plate is coupled, and wherein the wear plate includes an adhesive polymer to impede transmission of acoustic energy from the acoustic generator to the acoustic receiver through the wear plate.

2. The apparatus of claim 1, wherein the isolator includes high and low acoustic impedance layers.

3. The apparatus of claim 2, wherein the high and low acoustic impedance layers alternate.

4. The apparatus of claim 1, wherein the isolator is hemispherically shaped.

5. The apparatus of claim 1, wherein the acoustic generator includes a waveguide rod and wherein the isolator is cylindrically shaped, the waveguide rod being radially surrounded by the isolator.

6. The apparatus of claim 5, wherein the acoustic generator includes an acoustic signal generating element and wherein the waveguide rod acoustically couples the acoustic signal generating element to the wear plate.

7. The apparatus of claim 6, wherein the isolator includes high and low acoustic impedance layers stacked radially with respect to the waveguide rod.

8. The apparatus of claim 1, wherein the wear plate includes an acoustic generator portion joined to a receiver portion by the adhesive polymer, wherein the acoustic generator is acoustically coupled to the acoustic generator portion, and wherein the receiver is acoustically coupled to the receiver portion.

9. An apparatus comprising:
- an acoustic generator disposed in a housing, the acoustic generator including an acoustic signal generating element and an isolator;
- a receiver disposed in the housing adjacent to the acoustic generator;
- a fixative disposed in the housing to retain the acoustic generator and the receiver in the housing, the isolator to impede transmission of acoustic energy from the acoustic signal generating element to the receiver through the fixative; and
- a wear plate acoustically coupled to the acoustic generator and to the receiver, the wear plate to convey acoustic energy from the acoustic generator to a structure under test and to the receiver.

10. The apparatus of claim 9, wherein the isolator includes high and low acoustic impedance layers.

11. The apparatus of claim 10, wherein the high and low acoustic impedance layers alternate.

12. The apparatus of claim 9, wherein the isolator is hemispherical.

13. The apparatus of claim 9, wherein the acoustic generator includes a waveguide rod radially surrounded by the isolator.

14. The apparatus of claim 13, wherein the isolator includes high and low acoustic impedance layers stacked radially about the waveguide rod.

15. An apparatus comprising:
- a housing;
- a receiver portion of a wear plate supported by the housing;
- an acoustic receiver acoustically coupled to the receiver portion and disposed in the housing;
- an acoustic signal generating element disposed in the housing;
- a fixative disposed in the housing to retain the acoustic signal generating element, the acoustic receiver, and an isolator in the housing, the isolator to impede transmission of acoustic energy from the acoustic signal generating element into the fixative within the housing;
- an acoustic generator portion of the wear plate acoustically coupled to the acoustic signal generating element; and
- an adhesive polymer sandwiched between the acoustic generator portion and the receiver portion, the adhesive polymer to impede transmission of acoustic energy from the acoustic generator portion to the receiver portion.

16. The apparatus of claim 15, wherein the isolator includes high and low acoustic impedance layers.

17. The apparatus of claim 16, wherein the high and low acoustic impedance layers alternate.

18. The apparatus of claim 15, wherein the isolator is hemispherical.

19. The apparatus of claim 15, wherein the acoustic generator includes a waveguide rod radially surrounded by the isolator.

20. The apparatus of claim 19, wherein the isolator includes high and low acoustic impedance layers stacked radially about the waveguide rod.

* * * * *